US007014869B2

(12) United States Patent
Moore et al.

(10) Patent No.: US 7,014,869 B2
(45) Date of Patent: Mar. 21, 2006

(54) RAPID DEHYDRATION OF PROTEINS

(75) Inventors: Barry Douglas Moore, Glasgow (GB);
Marie Claire Parker, Glasgow (GB);
Peter James Halling, Glasgow (GB);
Johann Partridge, Glasgow (GB);
Howard Norman Ernest Stevens,
Stirlingshire (GB)

(73) Assignee: University of Strathclyde, (GB)

( * ) Notice: Subject to any disclaimer, the term of this patent is extended or adjusted under 35 U.S.C. 154(b) by 0 days.

(21) Appl. No.: 10/007,257

(22) Filed: Nov. 13, 2001

(65) Prior Publication Data
US 2002/0168414 A1    Nov. 14, 2002

Related U.S. Application Data

(63) Continuation of application No. PCT/GB00/01854, filed on May 15, 2000.

(30) Foreign Application Priority Data
May 13, 1999   (GB) ............................... GB9910975

(51) Int. Cl.
A61K 9/14       (2006.01)
A61K 9/16       (2006.01)
(52) U.S. Cl. .................. 424/490; 424/489; 424/491; 424/492; 424/493; 264/117; 264/118
(58) Field of Classification Search ................ 424/489, 424/490, 491, 492, 493; 427/2.14; 264/117, 264/115, 118
See application file for complete search history.

(56) References Cited

U.S. PATENT DOCUMENTS

| 5,198,353 | A | * | 3/1993 | Hawkins et al. ............. 435/188 |
| 5,219,554 | A | * | 6/1993 | Gowman et al. ............... 424/9 |
| 5,589,167 | A | | 12/1996 | Cleland et al. |
| 5,643,605 | A | * | 7/1997 | Cleland et al. ............. 424/489 |
| 5,753,219 | A | | 5/1998 | Cleland et al. |
| 5,994,314 | A | * | 11/1999 | Eljamal et al. ............... 514/44 |

FOREIGN PATENT DOCUMENTS

| EP | 0 356 239 | * | 2/1990 |
| GB | 2 131 941 | | 6/1984 |
| GB | 2 131 948 A | | 6/1984 |
| GB | 2131948 A | * | 6/1984 |
| WO | WO 97/34919 | * | 9/1997 |

| WO | WO-97/34919 | 9/1997 |

OTHER PUBLICATIONS

Bustos et al. "Stabilisation of trypsin like enzymes from antarctic krill: effect of polyols polysaccharides and proteins", Chem. Tech. Biotechnol. 1996, vol. 65, pp. 193-199.*
Randen et al. "Coprecipitation of Enzymes with water soluble starch-an alternative to freeze-drying", J. Pharm. Pharmacol, 1988, vol. 40, pp. 763-766.*
Lennart Randen, Jerker Nilson and Peter Edman; Coprecipitation of Enzymes with Water Soluble Starch—An Alternative to Freeze-drying; J. Pharm. Pharmacol; Jan. 25, 1998; pp. 763-766; vol. 40. (XP-000973058).
Ruben O. Bustos, Claudio R. Romo and Michael G. Healy; Stabilisation of Trypsin-Like Enzymes from Antarctic Krill: Effect of Polyols, Polysaccharides and Proteins; J. Chem. Tech Biotechnol; 1996; pp. 193-199; vol. 65; SCI, Great Britain. (XP-000973074).
T.R. Knochel, M. Hennig, A. Merz, B. Darimont, K. Kirschner and J.N. Jansonius; The Crystal Structure of Indole-3-glycerol Phosphate Synthase from the Hyperthermophilic Archaeon *Sulfolobus solfataricus* in Three Different Crystal Forms: Effects of Ionic Strength; J. Mol. Biol.; 1996; pp. 502-515; vol. 262; Academic Press Limited. (XP-000973153).
Alexander L. Dounce and George Mourtzikos; Isolation of Three Crystalline Proteins from Beef Liver After Partial Purification by Acetone Fractionation; Preparative Biochemistry; 1981; pp. 501-523; Fol. 11(5): Mercel Dekker, Inc. (XP-000973134).

* cited by examiner

Primary Examiner—Thurman K. Page
Assistant Examiner—S. Tran
(74) Attorney, Agent, or Firm—Alston & Bird

(57) ABSTRACT

The present invention relates to protein-coated micro-crystals and their method of preparation. The protein-coated micro-crystals may find particular application in preparing enzymes for use as biocatalysts; preparation of therapeutic proteins for use in pharmaceutical formulations; production of cleansing agents comprising enzymes; production of paints, varnishes, coatings, films and the like comprising proteins which impart protective and/or antifouling properties; production of films, polymers, inks, coatings, electrodes and/or optical materials comprising proteins for diagnostic kits and/or biosensor applications; use of proteins for studies of molecular recognition, molecular binding and inhibitor binding in non-aqueous media; and preparation of protein based food additives.

16 Claims, 9 Drawing Sheets

— 500nm

——500nm

——— 500nm

RAPID DEHYDRATION OF PROTEINS

CROSS-REFERENCE TO RELATED APPLICATIONS

This application is a continuation of International Application No. PCT/GB00/01854, filed May 15, 2000, which is hereby incorporated herein in its entirety by reference.

BACKGROUND

1) Field of the Invention

The present invention relates to water soluble particles comprising a biological macromolecule and a method of isolating a biological macromolecule from an aqueous solution with simultaneous dehydration of the protein, to provide protein biological macromolecule particles. The present invention also relates to water miscible organic solvents comprising the protein precipitated therein. The present invention may find particular application in preparing enzymes for use as biocatalysts; preparation of therapeutic proteins for use in pharmaceutical formulations; production of cleansing agents comprising enzymes; production of paints, varnishes, coatings, films and the like comprising proteins which impart protective and/or antifouling properties; production of films, polymers, inks, coatings, electrodes and/or optical materials comprising proteins for diagnostic kits and/or biosensor applications; use of proteins for studies of molecular recognition, molecular binding and inhibitor binding in non-aqueous media; and preparation of protein based food additives. Additionally the precipitated biological macromolecule may thereafter be dissolved in organic solvents for use in at least some of the aforementioned applications as well as in solid phase chemistry such as in the preparation of catalysts for attachment, cleavage and/or modification of compounds bound to an insoluble support.

2) Description of the Related Art

Proteins are used in a great variety of applications. However, generally speaking, for therapeutic purposes it is necessary to have a preparation of protein substantially free from impurities for use. There are many ways purification may be achieved such as by differential centrifugation, selective precipitation, solvent extraction and chromatographic processes. Additionally it is often desirable to dehydrate or dry the protein prior to use, that is remove water from the protein, in order to facilitate handling and/or improve shelf life.

Typically proteins may be dehydrated by freeze drying, vacuum drying or air drying techniques commonly known in the art. However these techniques suffer from a number of disadvantages. For example, the drying processes are not generally very quick and can be extremely expensive. Moreover, even freeze-drying may lead, particularly in the case of enzymes and fragile proteins, to a decrease in protein function. In order to preserve protein function additional stabilising excipients are often added. However, addition of stabilising excipients may in itself be undesirable particularly, for example, from a regulatory point of view for proteins to be used therapeutically.

U.S. Pat. No. 5,198,353 discloses a method of preparing a stabilised enzyme dispersion. There is described a method of coprecipitating a polymer and an enzyme from an aqueous solution in order to produce a finely dispersed enzyme for use in aqueous based liquid detergents. The polymer and enzyme are precipitated by the addition of either salts or organic solvents. When using an organic solvent as the precipitant it is disclosed that the organic solvent is added to the aqueous protein/polymer solution slowly with vigorous stirring in order to precipitate the protein. However the method and the amount of organic solvent added is such that there is not extensive and rapid dehydration of the protein.

U.S. Pat. No. 5,589,167 and U.S. Pat. No. 5,753,219 disclose excipient stabilisation of polypeptides treated with organic solvents. Polyols such as trehalose are disclosed as stabilising dry or aqueous polypeptides treated with organic solvents. However, there is no suggestion that the polyols could be used to coprecipitate with the protein on addition to an organic solvent or the relevance/importance of dehydrating the protein.

Randen et al (J. Pharm. Pharmacol., 1988, 40, 761–766) describes the coprecipitation of enzymes with water soluble starch as an alternative to freeze-drying. Starch of molecular weights 12 700 and 100 000 is disclosed as a coprecipitant of krill proteases when mixed with an organic solvent of acetone, ethanol or isopropanol. The particles produced after precipitation are described as irregular needles with low density with a size in the range of 200–700 μm. After drying the particles had to be further processed by milling or grinding to obtain a more uniform size distribution.

In a later paper citing the Randen et al paper, Bustos et al (J. Chem. Tech. Biotechnol., 1996, 65, 193–199) describe the use of additional polymeric compounds for use as coprecipitants. The polymeric compounds disclosed are hydrolysed collagen, casein and maltodextrins PSM 10 (12,100 Mw) and PSM 100 (100,000 Mw).

BRIEF SUMMARY OF THE INVENTION

It is amongst the objects of the present invention to provide a rapid process for isolating a protein from an aqueous solution wherein the protein is simultaneously dehydrated.

It is a further object of an embodiment of the present invention to provide bioactive molecule coated particles, such protein/nucleic acid coated micro-crystals.

In one aspect the present invention provides a method of preparing water soluble particles comprising the steps of:

a) preparing an aqueous solution comprising a coprecipitant and a biological macromolecule;

b) rapidly admixing the biological macromolecule/coprecipitant solution with an excess of a water miscible organic solvent such that the coprecipitant and bioactive molecule immediately coprecipitate from solution forming said particles; and c) isolating said particles from the organic solvent.

It is to be understood that the term "biological macromolecule" refers to a protein, peptide, polypeptide or the like, or nucleic acid such as DNA or RNA. Hereinafter reference to the biological macromolecule will generally be made by reference to a protein. However, it should be understood that such reference may also be equated with the other aforementioned biological macro molecules.

The term crystal-shaped is intended to mean a three-dimensional shape comprising planar surfaces and is thus distinguishable from generally spherical or spheroid shaped.

It is to be understood that the term "coprecipitant" refers to the compound which precipitates out of solution with the protein when added to the organic solvent and that the term "coprecipitate" when used as a noun, refers to a bioactive molecule-coprecipitant complex.

The protein to be isolated from the aqueous solution may be any protein or mixture of proteins. Typical proteins include enzymes such as subtilisin, chymotrypsin and proteases; blood proteins such as albumin, fibrinogen, thrombin and blood factors; and therapeutic proteins such as insulin, antibodies, blood and transport proteins, regulatory proteins, glycoproteins, lipoproteins, hormones and interferons.

The coprecipitant may be provided as a solid, for example as a powder, which is to be dissolved in the aqueous solution. Alternatively the coprecipitant may be in solution or suspension prior to dissolving in the aqueous solution. Typically the coprecipitant may be provided as a substantially saturated or highly concentrated solution.

The coprecipitant must be sufficiently soluble in the aqueous solution such that a suitable weight fraction can be obtained relative to the protein in solution. Desirably the coprecipitant should have a very much lower solubility in the chosen solvent than in the aqueous solution. Moreover, if well defined particles are required the coprecipitant should form crystals and coprecipitants with high melting points are therefore preferred. The concentration of coprecipitant required is a function of the amount of protein in the solution and the molecular mass of the protein. Generally speaking the solution prior to precipitation comprises a high molar ratio of coprecipitant to protein. Typically the coprecipitant: protein molar ratio may be greater than 50, preferably greater than 200, more preferably greater than 400.

Preferably the solid form of the coprecipitant (which may exist as a hydrate) should absorb very little water when exposed to humid environments. The coprecipitant should preferably have very low solubility in the organic solvent used for the coprecipitation.

The coprecipitant should also be chosen such that little or substantially none of the protein is denatured thereby.

Coprecipitants which may display at least some of the above desirable properties may be selected from:
inorganic salts, for example, potassium sulphate and potassium chloride;
sugars, polysaccharides, carbohydrates, polyols, and derivatives thereof, for example trehalose, typically with a molecular weight of less than 10,000 Da;
amino-acids such as glycine and arginine;
acid-base buffers, for example, potassium hydrogen phosphate, MOPS and POPSO;
zwitterionic compounds for example, betaines;
organic salts, for example choline and sodium benzoate;
compounds containing multiple basic groups, such as spermidine and salts thereof;
compounds containing multiple acidic groups, such as citric acid and salts thereof,
bile salts;
water soluble dyes;
polar or ionic polymers; and
polar or ionic dendrimers.

The protein-coprecipitant solution is admixed with a water miscible organic solvent or water miscible mixture of solvents, preferably one where the solvent or solvent mixture is fully miscible. It should be noted that the protein-coprecipitant solution is preferably added to the excess of organic solvent and not the other way around, in order to ensure that rapid dehydration of the protein/coprecipitant solution occurs. As a consequence protein-coated particles are reproducibly obtained. The excess of a fully water miscible organic solvent is such that the final water content of the solvent/aqueous solution is generally less than 30%, typically less than 20–10% and conveniently less than 5% v/v. In this manner the organic solvent should preferably initially contain less than 10% v/v water or be substantially dry, but may not necessarily be completely dry. Suitable organic solvents include methanol, ethanol, propanol, acetonitrile, tetrahydrofuran and acetone. In certain instances the organic solvent may be pre-saturated with the protein and/or coprecipitate to ensure than on addition of the aqueous solution the two components precipitate out together.

It should be understood that the term "admixed" refers to a process step where the organic solvent is mixed or agitated with the aqueous solution while the aqueous solution is added. The mixing needs to be efficient so that the protein is in contact with a mixture of intermediate composition ie. aqueous solution and organic solvent, for example between 25% and 60% solvent, for a minimal time. It will be appreciated by the skilled reader that admixing therefore does not mean the entire aqueous solution needs to be added to the organic solvent quickly and substantially in a single step and could for example be added dropwise.

Moreover, the protein-coprecipitant solution is preferably added to the excess organic solvent. This entails the smaller volume of protein-coprecipitate solution being added to the larger volume of the excess of organic solvent such that rapid dilution of water from the protein-coprecipitate solution into the organic solvent occurs with an accompanying rapid dehydration of the protein and formation of protein-coated particles. Furthermore, the aqueous solution may be added to the organic solvent using a wide range of methods such as a continual stream, drop-wise or as a spray or mist.

The temperature at which the precipitation is carried out can be varied. For example, the aqueous solution and the solvent could be either heated or cooled. Cooling may be useful where the protein is fragile. Alternatively the solvent and aqueous mixtures could be at different temperatures. For example the solvent could be held at a temperature below the freezing point of the aqueous mixture. Moreover the pressure could also be varied, for example higher pressures might be useful to reduce the volatility of the solvent.

Upon admixing the protein-coprecipitant solution to the excess of organic solvent, precipitation of the protein and coprecipitant occurs substantially instantaneously. However, mixing of the solvent/aqueous solution may be continued for a short time, for example for between 5–15 minutes in order to ensure as much of the protein is precipitated as possible.

With time the coprecipitate will settle and allow recovery of the protein-coated particles. The coprecipitate may however be subjected to, for example, centrifugation and/or filtration in order to more rapidly recover the precipitated protein-coated particles. A simple drying procedure may be used to evaporate any residual solvent to leave a solvent free dry protein-coated particles precipitate.

It has advantageously been found that the precipitated protein-coated particles may be stored in the organic solvent and that the protein displays extremely good retention of activity and stability over an extended period of time. Moreover, since the precipitated protein is typically stored in the organic solvent, it will therefore be resistant to attack by bacteria, thus increasing its storage lifetime.

If necessary, the precipitated protein-coated particles may be further dehydrated by further washing with fresh organic solvent.

The precipitated protein may be redissolved in an aqueous solution prior to use. Alternatively the precipitated protein may be dissolved directly into an organic solvent. This may be achieved for example using an organic soluble ion-pairing agent, non-covalent binding of amphiphilic compounds such as non-ionic detergents or covalent attachment of organic soluble groups such as PEG, long chain alkyl chains, dendritic molecules or polymers.

Previous wisdom has taught where ion pairing agents have been used to solubilise enzymes in organic solvents, that the protein be in aqueous solution when the ion pairing takes place. The present method however allows ion pairing to take place under very low water conditions. This it should be noted has several potential advantages: for example, interfacial protein denaturation may not occur; electrostatic and/or polar interactions may be stronger; direct solubilisation into polar solvents is possible; water sensitive ion pairing agents can be used; mixtures of different ion pairing agents can be used; the protein ionisation state can be controlled with solid-state acid-base buffers that do not interfere with the ion pairing process; the process can be carried out at controlled water activity; no lyophilisation steps are required and the solubilisation process requires only simple equipment and is easy to scale up.

The method described herein may also allow organic soluble components present in the aqueous solution to be separated from the protein. For example a buffer such as Tris which in its free base form is soluble in an organic solvent like ethanol may be separated from the protein during precipitation. However, it may be necessary to convert all the buffer to the free base by the addition of another organic soluble base to the aqueous solution or organic solvent. Thus the present invention also discloses a method of removing undesirable components from the protein, such that the undesirable components are not coprecipitated with the protein and so remain dissolved in the organic phase. This may be achieved by the inclusion of additives, such as acids, bases, ion-pairing agents and chelating agents in the aqueous or organic solvent prior to protein precipitation.

The present invention may be used for a great many applications. For example, enzyme-coprecipitant particles may be used as biocatalysts, particularly for reactions in low water systems, organic solvents and supercritical fluids.

The good retention of catalytically active enzyme structure within the fine, dry enzyme-coprecipitate particles provide significant advantages for biocatalysis in low water systems, organic solvents and supercritical fluids when compared with lyophilised powders. Applications include biocatalysis in the organic synthesis of fine chemicals and pharmaceutical intermediates, agrochemicals, detergents, fats, emulsifiers, food-stuffs, vitamins, sweetners, flavours and perfumes, monomers and polymers and modification of synthetic and natural polymers. Other applications include combinatorial biocatalysis for use in for example identification of new lead compounds, enzyme catalysed solid-solid synthesis, peptide synthesis and high temperature and low temperature biocatalysis. In addition biocatalysts in enzyme-coprecipitate particles can be used for the degradation of chemicals and polymers including those found in toxic waste, chemical and biological weapons, domestic and industrial waste and waste for natural sources. Enzyme catalysed processes often have the advantage over chemical methods of imparting regiospecificity, enantiospecificity and stereospecificity.

Additionally the present method allows the preparation of therapeutic bioactive molecules for pharmaceutical formulations.

The method produces fine dry particles containing protein and a coprecipitant. Thus, in a further aspect the present invention provides water soluble crystal-shaped particles of less than 50 $\mu$m comprising a coprecipitant and dehydrated biological macromolecule located at or close to an outer surface of the particle.

It is to be understood that the term "dehydrated biological macromolecule" refers to a biological macromolecule substantially unassociated with water and the term "coprecipitant" is as previously defined.

Typically, the dehydrated biological macromolecule is located at or near the surface of the coprecipitant. Generally speaking, the biological macromolecule retains a native or near native configuration when dehydrated ie. it is not irreversibly denatured. For example, if the biological macromolecule is an enzyme then it is to be expected that the enzyme retains most of its activity when kept in solvent and/or reconstituted in aqueous media.

Additionally in the dehydrated state enzymes and other biocatalysts are able to efficiently catalyse reactions under low water conditions such as in organic solvents. The retention of native conformation on dehydration can be probed for example by carrying out an active site titration in a low water organic solvent.

Preferably, the co-precipitant within the particles is crystalline. The crystalline precipitant provides a dense core with the dehydrated protein located at or close to the particle surface. This minimises diffusion limitations so that the dehydrated state of the biological macromolecule is easily accessible for example to solvent, reagents, substrates, stabilisers or modifiers.

Generally, the size of the particles is less than 10 $\mu$m and is, for example, less than 5–1 $\mu$m.

Typically the particles within a coprecipitate have fairly uniform dimensions and exhibit a particular regular crystal-shape such as for example cubes, rhomboids, plates and needles. The crystal-shape of the coprecipitate varies with both coprecipitant and protein. The flat surfaces exhibited by crystal-shaped particles make them well suited for carrying out scanning probe microscopy and surface force microscopy such as for example atomic force microscopy. Using such techniques the dehydrated protein can be imaged on the surface of the particles and its distribution, organisation and structure can be probed. This can be used to probe the tertiary and quaternary structure of proteins such as membrane proteins where it is difficult to obtain structures by x-ray crystallography. It is to be understood that the coprecipitate crystals can be produced using a wide variety of coprecipitants as previously described.

Generally these particles can be redissolved rapidly in aqueous solution or easily form suspensions and can be reproducibly dispensed for example using pipettes (by hand or automated) and so are attractive as a starting point for formulating proteins for medical applications. If a therapeutic protein is employed the particles can be used in the production of many different types of drug formulations including tablets, creams, powders, gels, foams, aerosols, suspensions, tapes and patches. The bioactive molecule coated particles may be particularly suited for transport across mucosal surfaces and may therefore be suitable for administration via inhalation. The dimensions of the particles make them particularly suited for pulmonary administration via inhalation into the lower alveolar regions of the lungs where absorption into the blood-stream is most efficient. For this application particles in the range 0.5 microns to 5 microns are most desirable. This may require mixing of the protein-coprecipitant particles with additional excipients to act for example as fillers, bulkers and/or binders. The particles can be used as the starting point for further manipulations including encapsulation into natural and synthetic polymers for the production of beads, films, fibres, bandages and plasters. Coatings can be applied to the surfaces of the particles to alter their solubility, processability and dispersability. Coatings are useful for changing rates of drug delivery and altering the surface properties of the particles.

The present method also allows the production of cleansing agents containing enzymes.

As aforementioned, the method produces fine dry particles containing protein and a coprecipitant that can be redissolved rapidly in aqueous solution and are thus also attractive for the production of cleansing agents that contain enzymes. Enzymes can be incorporated into tablets, creams, powders, gels, foams, aerosols and suspensions to be used for cleansing. This may require mixing of the protein-coprecipitant particles with additional excipients to act for example as fillers, bulkers and binders. Examples include a) preparation of tablets containing enzymes such as proteases or peroxidases for cleaning contact lenses and b) preparation of tablets, powders or suspensions containing enzymes such as proteases, lipases or cellulases to include in washing powders for fabrics or dish washers. The particles can be used as the starting point for further manipulations including encapsulation into natural and synthetic polymers. Coatings can be applied to the surfaces of the particles to alter their solubility, processability and dispersability. Coatings are useful for altering the surface properties of the particles and to change their behaviour in solvents or on resuspension in water.

The method may be used in production of paints, varnishes, coatings and films containing proteins to impart protective or antifouling properties.

The fine protein-coprecipitant particles can be dispersed in a carrier medium in a similar way to that employed for pigments for the production of paints, varnishes, coatings and films. If enzymes such as proteases, lipases or cellulases are used the resultant coatings may have antifouling properties preventing the attachment of live biological organisms such as bacteria, yeasts, fungi, micro-organisms and molluscs.

The production of films, polymers, inks, coatings, electrodes and optical materials containing proteins for diagnostic kits and biosensor applications may also be achieved using the present method.

The fine protein-coprecipitant particles can be dispersed into a carrier medium such as a paint or ink and used to produce films or coatings on test strips, electrodes or optical materials. These can then be used as the active element in diagnostic kits and biosensor applications.

In addition the use of protein-coprecipitant particles prepared according to the present invention may be used for studies of molecular recognition, molecular binding, molecular imprinting and inhibitor binding in non aqueous media.

The protein retains native like structure in the protein-coprecipitant particles and enzymes retain high catalytic activity. The precipitates can therefore be used for quantitative studies of molecular recognition, molecular binding and inhibitor binding in non-aqueous media. This can be used for the improvement of inhibitor and substrate design for applications in for example medicine, vetinary science and agriculture.

Moreover protein-coprecipitant particles of the present invention may be as protein based food additives.

The precipitation solvent and coprecipitants used can be chosen to be non-toxic for ingestion or inhalation by humans or animals and so the method can be used for rapid and cheap production of dry protein based food additives or pharmaceuticals.

BRIEF DESCRIPTION OF THE SEVERAL VIEWS OF THE DRAWINGS

The present invention will now be further described by way of example only and with reference to the accompanying figures which show.

DETAILED DESCRIPTION OF THE INVENTION

EXAMPLE 1

Preparation of Subtilisin

Figure 1:
FIG. 1 is a typical image obtained by transmission electron microscopy of protein-coprecipitant particles isolated by the method of the present invention.

Subtilisin Carlsberg (type VIII: bacterial, from *bacillus lichenformis*, crystallised and lyophilised was obtained from Sigma, Poole, U.K.). 2 mg of subtilisin (as received) was dissolved in 50 $\mu$l buffer (Tris, 10 mM, pH 7.8,) to which, 150 $\mu$l of saturated solution of a coprecipitant, potassium sulphate, $K_2SO_4$, (120 gl$^{-1}$) was added. The final concentration of protein in the solution was 0.37 mM and the molar ratio of $K_2SO_4$:enzyme in the precipitate was approximately 1400 corresponding to ~11% by weight subtilisin.

200 $\mu$l of the coprecipitant-enzyme solution was pipetted, immediately after preparation, into 3 ml of propanol contained in a 7 ml glass vial. The solution was pipetted using a Gilson micropipette in approximately 4×50 $\mu$l portions while agitating with an orbital shaker, shaking at approximately 100 rpm. The addition of the aqueous solution to the dry organic solvent results in immediate co-precipitation of both the $K_2SO_4$ and protein. The vial containing the very fine dispersion of coprecipitant-enzyme solid was capped and shaken for a further 15 min. at an increased speed of 800 rpm; the water content of the resultant mixture was approximately 6.25% v/v. The vial was removed from the shaker and the precipitate allowed to settle. After the precipitate settled (~30 min), the supernatant was removed, leaving behind approximately 100 $\mu$l of the original solvent. (Settling can be speeded by gentle centrifugation for approximately 1 minute. A further 3 ml of the solvent was added and the mixture shaken for 15 min on the orbital shaker resulting in a final water content of approximately 0.2% v/v. The mixture was left to settle or centrifuged and most of the solvent removed to leave the salt-enzyme precipitate suspended in approximately 100 $\mu$l of solvent. The suspension can be stored as it is or further treated depending upon the application.

Potassium chloride, KCl, (saturated solution, 281.5 gl$^{-1}$) was also tested as a coprecipitant following the same procedure as described above for $K_2SO_4$. Using the same concentration of enzyme and same volume of saturated salt solution results in a molar salt:enzyme ratio of ~7500 corresponding to ~5% subtilisin by weight. It is found that for precipitation into acetonitrile($CH_3CN$) the KCl-enzyme mixture was not suitable as it forms a two-liquid phase mix.

Amino Acids As Co-Precipitants

Glycine, lysine, arginine and glutamic acid were obtained from Aldrich U.K. and tested as coprecipitants.

Precipitation:

4 mg subtilisin in 100 $\mu$l saturated solution of amino-acid co-precipitant were precipitated into 6 ml 1-PrOH. The obtained suspensions were centrifuged (distributed into Eppendorf tubes, 6×1 ml) and washed once with 1-PrOH (1 ml per Eppendorf tube).

Precipitated samples were also prepared with D(+) trehalose ($\alpha$-D-glucopyranosyl-$\alpha$-D-glucopyranoside) obtained from Sigma (Poole, U.K.) as the coprecipitant. The trehalose was dissolved in distilled water to saturation (~76 g $l^{-1}$), and the preparation carried out in an identical manner, to that described above. The final molar ratio of sugar:protein was 406 corresponding to 15% by wt subtilisin.

General Appearance And Properties Of Coprecipitant-Subtilisin Precipitates

A very fine white precipitate forms immediately upon addition of the protein-coprecipitant solution to the organic solvent: individual particles are extremely small and take some time to settle in the solvent. The size of the particles is visibly different from coprecipitant precipitated without protein present (for $K_2SO_4$, KCl and trehalose) which, in this case, are larger. If a protein solution containing no coprecipitant is added to solvent again the particle morphology is very different: a stringy white precipitate forms. Precipitated $K_2SO_4$-subtilisin particles show no obvious change of morphology or aggregation over several weeks when left in the solvent. The $K_2SO_4$-subtilisin coprecipitate can be easily re-dissolved in aqueous solution, pH 7.8, or distilled water for assays in aqueous solution. Dissolution can be achieved by either dissolution from a small volume of propanol solution (typically less than 50 $\mu$l of 1-propanol) into 1 ml of buffer, pH 7.8 or by drying the precipitate and redissolution into aqueous.

With the amino-acids as coprecipitants in all cases a fine white precipitate was obtained. Electron microscopy showed that with glycine needle shaped particles were obtained.

EXAMPLE 2

Testing of Various Organic Solvents

The solvents so far tested for the precipitation are shown in Table 1. They were all obtained from Aldrich, Co. and were of analytical/spectrophotometric grade (99+%).

TABLE 1

Water content of solvents used for precipitation. Water level was assayed by Karl Fischer automatic water titration using a Metrohm 684F Coulometer (Metrohm, Switzerland).

| Solvent | Water content (% w/w) as received |
|---|---|
| Methanol | 0.13 |
| Ethanol | 0.05 |
| Propanol | 0.14 |
| Acetonitrile | 0.013 |
| Acetone | 0.08 |

Measuring The Bioactivity Of Coprecipitant-Enzyme Preparations In Various Organic Solvents It is well known that serine proteases such as subtilisin Carlsberg, or $\alpha$-chymotrypsin exhibit catalytic activity when suspended in organic solvents. This type of system can therefore be used as a convenient measure of how the bioactivity of a protein is affected by the dehydration process. By assaying, under identical conditions, a range of enzyme-coprecipitant precipitates isolated from different solvents it was possible to determine what solvent and coprecipitant resulted in the least protein denaturation. In addition the results could be compared to those obtained with freeze dried enzyme powders. The enzyme-coprecipitant suspensions prepared as described above were rinsed once with the assay solvent to remove residual precipitation solvent then assayed as described below. The results of the experiments are shown in Tables 2 and 3.

The assays of catalytic activity were carried out in two different solvents,($CH_3CN$ and n-hexane), containing a controlled amount of water. Substrates were; N-acetyl-L-phenylalanine ethyl ester (10 mM) and 1-propanol (1 M). With $CH_3CN$ as the reaction solvent N-acetyl-L-tyrosine ethyl ester (10 mM) was the chosen substrate and 1 M 1-propanol as before. Enzyme concentration was 1 mg/ml. Typically, the reaction vial contained 2 ml of solvent in a 4 ml screw-cap vial with teflon liner. The reaction vials were shaken for the duration of the experiment on an orbital shaker at approximately 250 rpm. Periodically 50 $\mu$l of the solvent mix was removed and diluted into the appropriate solvent (450 $\mu$l). These vials were then stored at −4° C. for gas chromatographic (G.C.) analysis at a later date.

TABLE 2

Catalytic activity of subtilisin Carlsberg preparations in dry n-hexane. The precipitations were carried out as in section 2.0 but using subtilisin dissolved in water with no buffer is present.

| Coprecipitant | precipitating solvent | relative enzymic activity | Notes |
|---|---|---|---|
| None | none | 1 | freeze-dried powder |
| $K_2SO_4$ | acetonitrile | 31.6 | salt at saturation |
| $K_2SO_4$ | acetone | 11.6 | salt at saturation |
| $K_2SO_4$ | methanol | 7.5 | salt at saturation |
| $K_2SO_4$ | ethanol | 18.6 | salt at saturation |
| $K_2SO_4$ | ethanol | 7.1 | saturation/5 |
| $K_2SO_4$ | acetonitrile | 1.4 | saturation/5 |
| KCl | acetone | 10 | salt at saturation |
| KCl | acetonitrile | 1.7 | salt at saturation |
| KCl | ethanol | 5.58 | salt at saturation |
| KCl | methanol |  | salt at saturation |
| KCl | ethanol | 7.3 | saturation/3.8 |
| KCl | acetone | 4.1 | saturation/3.8 |

From Table 2, it can be seen that generally, using $K_2SO_4$ as a coprecipitant results in higher catalytic activity in n-hexane, than that found using KCl. When $K_2SO_4$ was used at a concentration 5× lower than saturation reduced activity was observed. Additionally, as mentioned previously KCl-enzyme (aq) when precipitated into acetonitrile ($CH_3CN$) forms a two-phase mix. In nearly all cases the coprecipitant-enzyme precipitate showed superior bioactivity than lyophilised powder.

TABLE 3

Catalytic activity of preparations of subtilisin Carlsberg and chymotrypsin in acetonitrile containing 0.5% water. The enzymes were precipitated with buffer present as described in Example 1.

| Coprecipitant | precipitating solvent, wash solvents | Relative rate | Notes[a] |
|---|---|---|---|
| None | none | <0.01 | sub, chy, lyophilised |
| $K_2SO_4$ | PrOH, x1PrOH x1 AcN | 4.2 | sub, $K_2SO_4$, sat |
| KCl | PrOH, x1PrOH x1 AcN | 8.6 | sub, KCl sat |
| KCl | PrOH, x1PrOH x1 AcN | 5.6 | sub, Kcl sat/3.8 |
| $K_2SO_4$ | PrOH, x1PrOH x1 AcN | 0.8 | chy, $K_2SO_4$, sat |
| KCl | PrOH, x1PrOH x1 Acn | 0 | chy, KCl sat |
| KCl | PrOH, x1PrOH x1 AcN | 1.3 | chy, KCl sat/3.8 |
| $K_2SO_4$ | AcN, x1 AcN | 2.1 | sub, $K_2SO_4$, sat |
| KCl | AcN, x1 AcN | 1.3 | sub, KCl sat |
| KCl | AcN, x1 AcN | <0.4 | sub, KCl sat/3.8 |
| $K_2SO_4$ | AcN, x1 AcN | 1.76 | chy, $K_2SO_4$, sat |
| KCl | AcN, x1 AcN | <0.4 | chy, KCl sat |
| KCl | AcN, x1 AcN | <0.4 | chy, KCl sat/3.8 |

[a] chy = chymotrypsin, sub = subtilisin

It can be seen from Table 3 that the coprecipitant-enzyme precipitates are much more active in AcN than lyophilised powders indicating much better retention of the bioactive conformation.

Activity Assay Of Amino-Acid Precipitates:

The precipitate from 1 eppendorf (0.67 mg enzyme) prepared as described previously was used for each enzyme assay. Activity was measured by HPLC following the transesterification of N-acetyl-L-tyrosine ethyl ester (10 mM) and 1-propanol (1 M) with acetonitrile/1% $H_2O$ as solvent.

Figure 9:
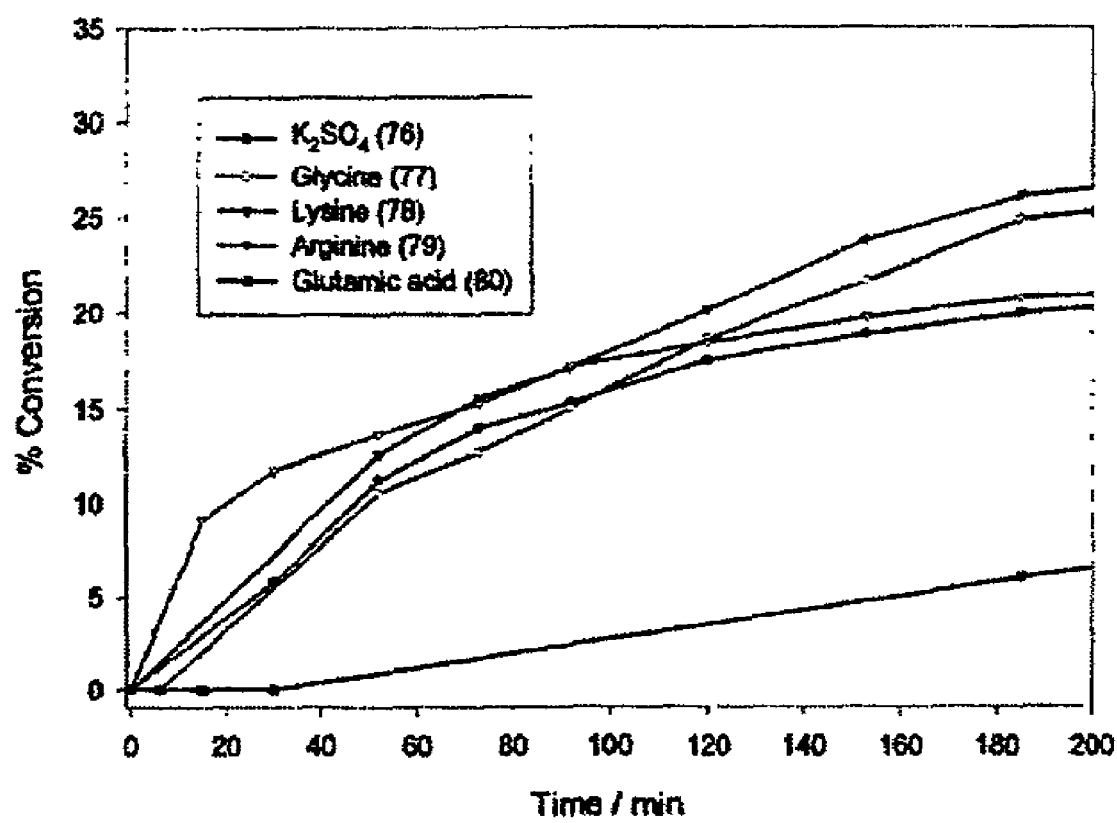
FIG. 9 shows the effect of various amino acid co-precipitants, on the activity of subtilisin.

FIG. 9 shows the effect of various amino acid co-precipitants, on the activity of subtilisin in comparison to $K_2SO_4$. Arginine led to an increased initial rate, whereas glycine and lysine increased the final conversion after 3 hours slightly. With glutamic acid the transformation was much slower and with lypohilised enzyme less than 1% conversion was observed. These results are generally as expected because amino-acids can act as solid-state acid-base buffers in organic solvents. Lysine and glycine are able to mop up protons produced by hydrolysis by-product. Glutamic acid will increase the protonatation state of subtilisin so that it becomes less catalytically active.

EXAMPLE 3

Redissolution of $K_2SO_4$-Subtilisin Carlsberg and Activity in Aqueous Solution Precipitated $K_2SO_4$-subtilisin could be fully and rapidly redissolved in buffer indicating no irreversible denaturation had occurred during dehydration. The activity of subtilisin Carlsberg in aqueous solution was assayed using the following procedure: Assays were carried out using ρ-nitrophenyl acetate (97%, Aldrich, Poole, U.K.) which releases the chromophoric nitrophenol when hydrolysed. The reaction rate was monitored by U-V spectrophotometry, detection wavelength (λ)=400 nm. A 1 ml quartz cell, contained 200 μl of a 3 mM solution of ρ-nitrophenyl acetate (97%), Aldrich, U.K.); 800 μl of tris buffer, pH 7.8 and an aliquot (20 μl) of the $K_2SO_4$-subtilisin, re-dissolved into buffer solution (1 mg/ml).

$K_2SO_4$-subtilisin precipitate left suspended in propanol for 72 hrs was found to have retained 100% activity when re-dissolved back into aqueous. Similarly upon air drying, for two days $K_2SO_4$-subtilisin dissolved back into water immediately and was found to be 100% active. A qualitative test of activity with ρ-nitrophenyl acetate also showed that after 3 weeks of storage over $P_2O_5$, (room temp) the $K_2SO_4$-subtilisin could be easily redissolved in buffer solution, pH 7.8, and remained catalytically active.

EXAMPLE 4

Active Site Titration of Precipitated Enzyme in Propanol

Samples of c.a. 2 mg subtilisin Carlsberg and c.a. 18 mg potassium sulphate dissolved in 200 μl 2.5 mM Tris buffer, pH 7.8, were coprecipitated into 3 ml propanol containing 1% water using the method described in Example 1. On settling of the particles the majority of solvent was decanted off and the samples were rinsed once with 3 ml of the same solvent. Half the samples were then incubated with a 10 mM solution of the active site titrant phenylmethane sulfonyl fluoride (PMSF) in 3 ml propanol for 1 hour. Most of the titrant mixture was decanted from the incubated samples and they were rinsed three times with 3 ml aliquots of pure propanol. The catalytic activity of the PMSF treated and non-treated samples were measured in aqueous solution using the standard assay described in Example 3. The results were then compared to those of non-precipitated subtilisin Carlsberg. The assays showed that the normal precipitated enzyme retained >95% activity while that treated with PMSF exhibited <10% of the initial activity. Control experiments showed that the rinsing procedure efficiently removes excess PMSF and no significant titration takes place during the dissolution of the precipitate back into water. This suggests that the loss in catalytic activity therefore arises from titration of the enzyme active sites by PMSF while the protein is dehydrated and suspended in the solvent. The results provide evidence that the >90% of the subtilisin molecules in the precipitate retain a biologically active conformation following the dehydration and precipitation process.

EXAMPLE 5

Transmission Electron Microscopy

Aliquots of a standard protein-coprecipitant particles of subtilisin Carlsberg/$K_2SO_4$ suspended in propanol were dropped onto carbon coated electron microscope grids. The samples were air dried and then examined using a Jeol JEM 1200EX transmission electron microscope (Jeol Tokyo, Japan).

Figure 2:
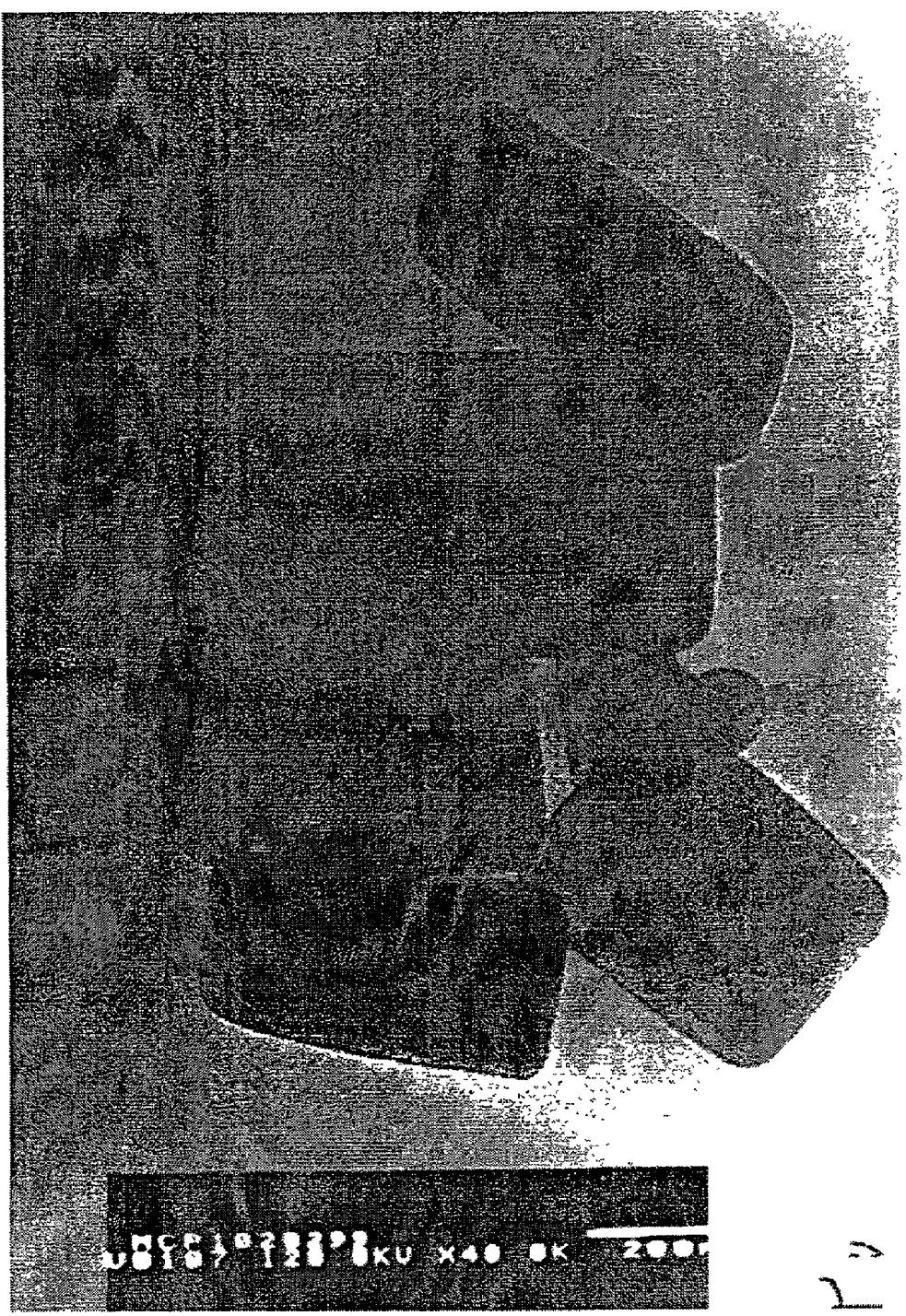
FIG. 2 is a high-magnification image of the protein-coprecipitant particles illustrated in FIG. 1.

FIGS. 1 and 2 show typical images obtained. It can be see that the protein-coprecipitant forms regular shaped crystals. From the scale bars (500 nm and 200 nm respectively) the protein-coprecipitant particles are observed to have dimensions generally less than 2 microns. In the higher magnification image a thin surface coating can be observed on the crystals. It is believed that this layer consists of layers of the protein which is excluded from the crystal lattice during the crystallisation process. In the absence of any protein, similar shaped but larger crystals are obtained via the precipitation procedure.

Figure 3:
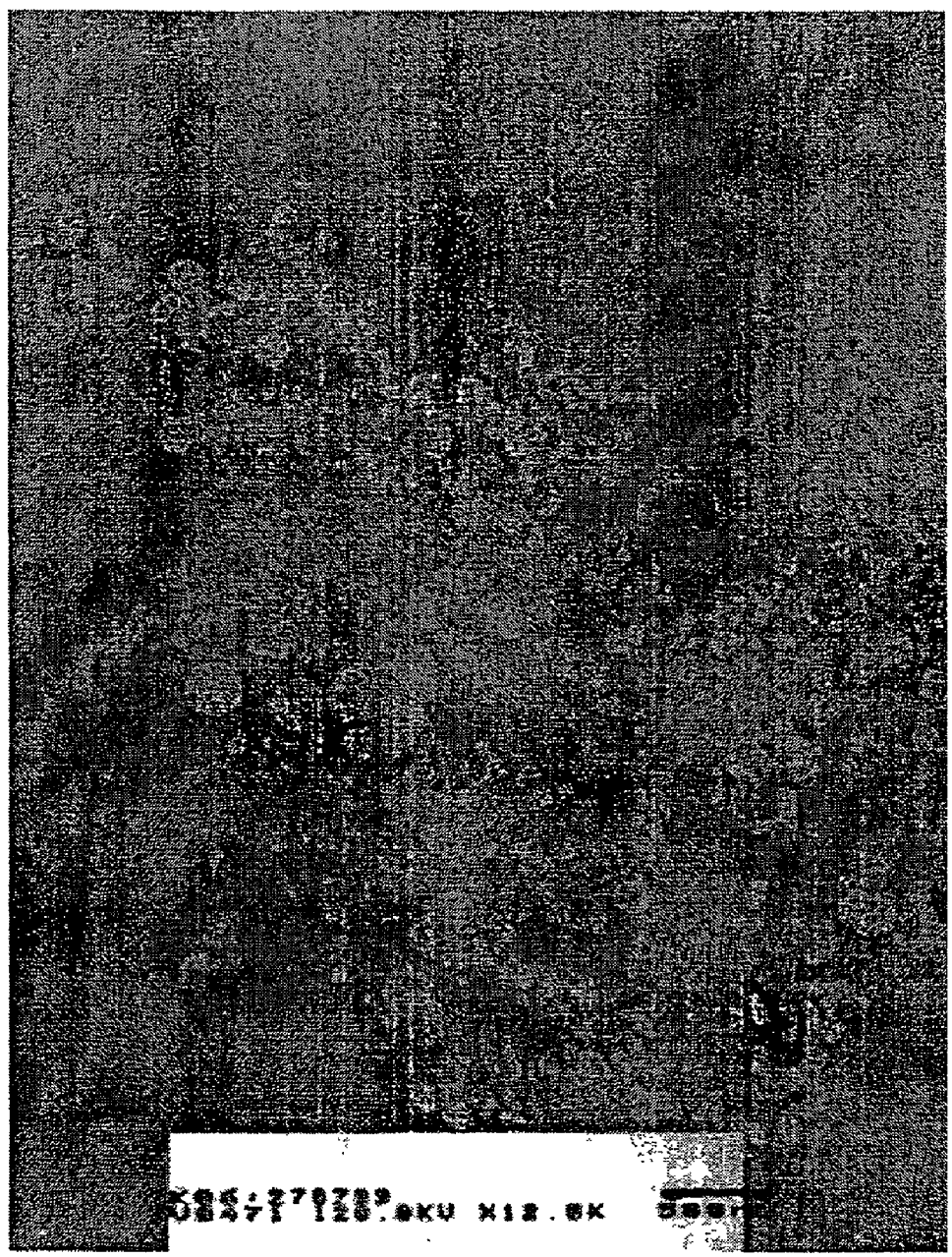
FIG. 3 shows subtilisin precipitated into 1-PrOH with no salt present.
Figure 4:
FIG. 4 shows subtilisin coprecipitated into 1-PrOH containing 26% $H_2O$.
Figure 5:
FIG. 5 shows the effect of 1-PrOH addition to aqueous phase solution of subtilisin and $K_2SO_4$.

FIG. 3 shows the agglomerates of protein which are formed when subtilisin is precipitated without salt. This is easily compared to the protein-coated crystals (see FIG. 4) obtained when subtilisin is coprecipitated with $K_2SO_4$ in 1-PrOH. As can be seen in FIG. 5 if 1-PrOH is added to an aqueous solution of subtilisin and $K_2SO_4$ different structures are formed with protein strands being attached between salt crystals (ie. protein is not coated on the crystals).

EXAMPLE 6

Figure 6:
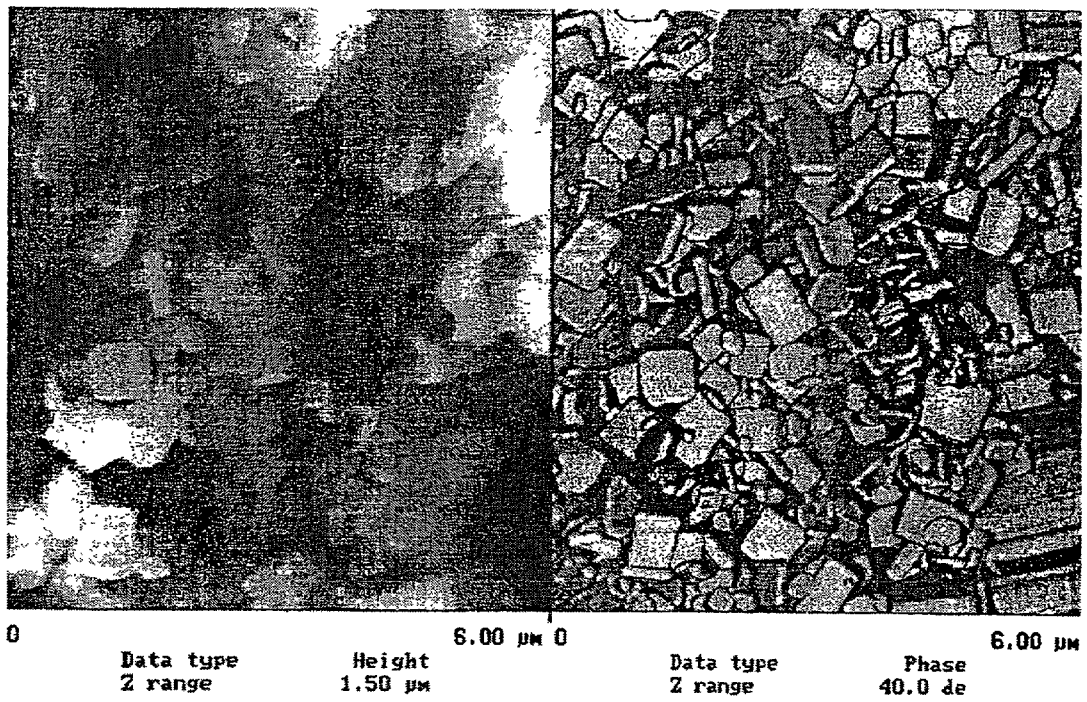
FIG. 6 shows AFM images of subtilisin coated crystals of $K_2SO_4$.
Figure 7:
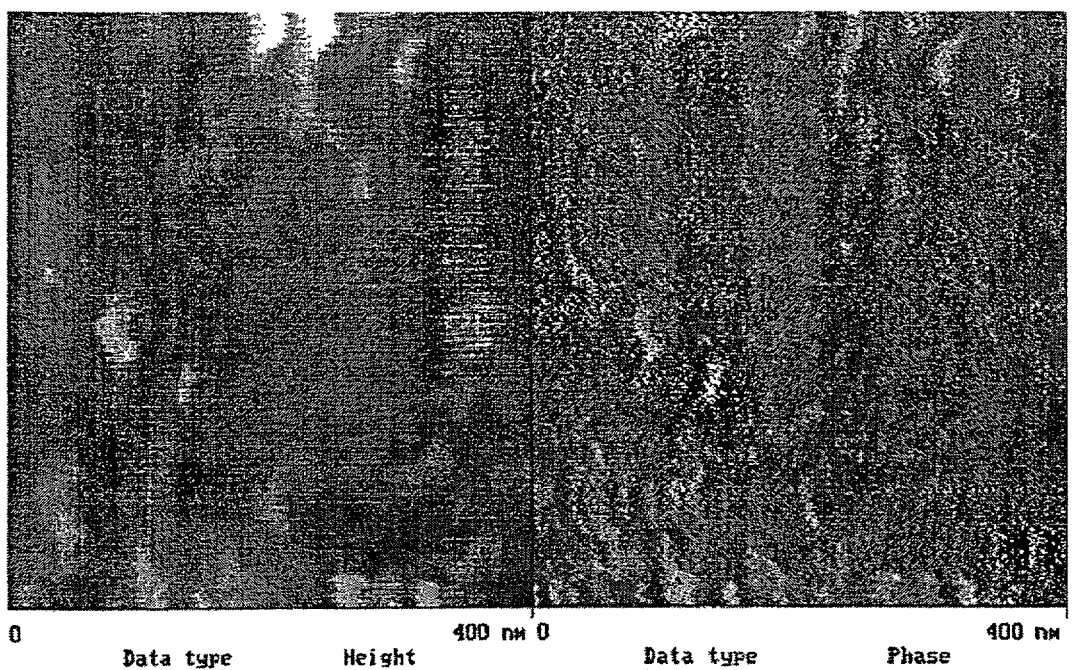
FIG. 7 shows AFM images of the surface of a single crystal of $K_2SO_4$ in the absence of subtilisin.

Surface Microscopy of the Coprecipitate Obtained from a Mixture of Subtilisin And $K_2SO_4$ It was found that coprecipitation of a mixture of subtilisin and $K_2SO_4$ in the manner described in Example 1 provided regular crystals with large flat surfaces as shown above by electron microscopy. This makes them well suited for study by scanning force microscopy (SFM) which can be used to study the detailed topography of surfaces. If the underlying surface is flat scanning force microscopy techniques can also be used to study molecules located on a surface. In this study a Digital Nanoscope atomic force microscope was used to examine the coprecipitate using tapping-mode amplitude-phase distance measurements. FIG. 6 shows an image of a collection of crystals taken with a scan size of 6 $\mu$m×6 $\mu$m and a z-height of 1.5 $\mu$m. It can be seen that the crystals have fairly uniform dimensions and exhibit regular tablet-like shapes with flat planar surfaces. At this scale images of the crystals formed by $K_2SO_4$ precipitated without protein present were similar. Higher resolution images, were then obtained of parts of faces of individual crystal precipitated in the absence and presence of protein. FIG. 7 shows a representative image of a 400 nm×400 nm area of a crystal obtained in the absence of protein. It can be seen from the z-axis range of 4 nm that the surface is quite featureless and fairly flat.

Figure 8:
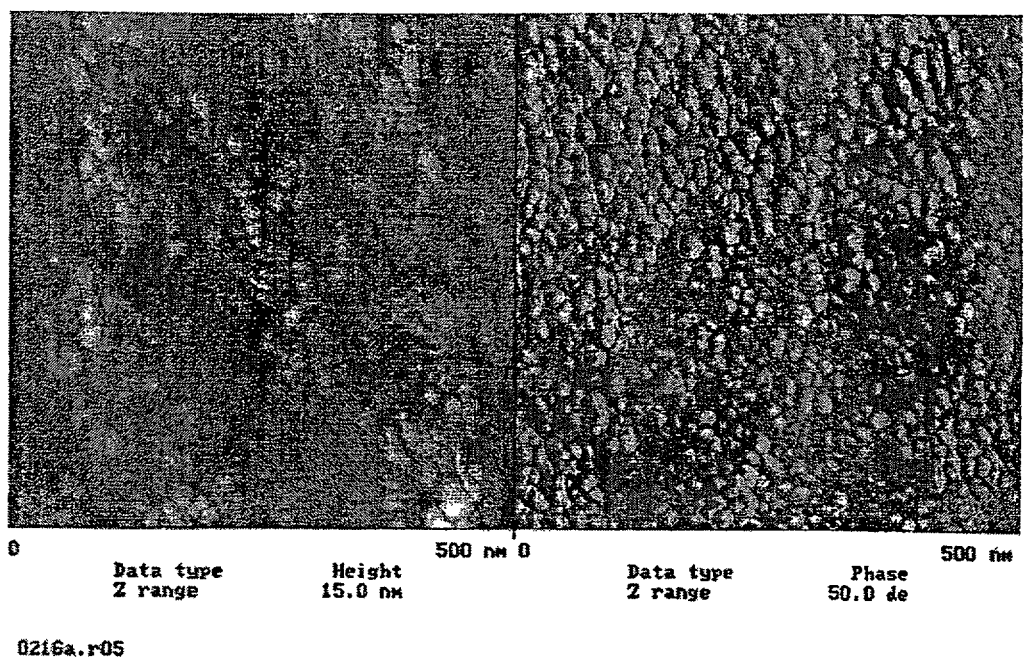
FIG. 8 shows AFM images of the surface of a single crystal of $K_2SO_4$ coated with subtilisin.

FIG. 8 shows a representative image of a 500 nm×500 nm area of a crystal obtained by coprecipitation of the salt with protein. It can be seen immediately from the increased z-height range of 15 nm that the surface is much rougher. Closer inspection shows that the surface is coated with a layer of protein particles of nanometre dimensions.

EXAMPLE 7

Precipitation of Insulin

Insulin from bovine pancreas was obtained from Sigma, UK (Product Number I-5500).

Precipitation:

2 mg insulin was dissolved in 200 $\mu$l HCl (0.010 M), and the pH increased by adding 333 $\mu$l of NaOH (0.010 M). The insulin solution was mixed with 150 $\mu$l saturated $K_2SO_4$ solution and precipitated into 5.317 ml PrOH containing 1.3% $H_2O$. The obtained suspension was centrifuged, and washed once with 1-PrOH/1.3% $H_2O$. The fine particles were essentially of the same appearance as obtained with subtilisin (see Example 1).

Circular Dichroism Spectra of Insulin

The following samples were measured on a JASCO J-600 spectropolarimeter under PC control.

insulin from bottle insulin co-precipitated with $K_2SO_4$ as described above.

The spectra obtained were very similar both to each other and to a literature spectrum showing that insulin substantially retains its native structure following precipitation and redissolution.

EXAMPLE 8

Precipitation of DNA

DNA-genomic, ultrapure from calf thymus, with average molecular weight=8.6 MDa corresponding to approximately 13 Kbase pairs was bought from Sigma.

Precipitation:

0.5 unit of DNA was dissolved in 100 $\mu$l and mixed with 300 $\mu$l of a saturated $K_2SO_4$ solution. This was added to 4.5 ml of 1-PrOH (previously dried over molecular sieves) resulting in immediate formation of a fine precipitate. The suspension was shaken at 600 rpm for 2 mins, allowed to settle, and centrifuged in eppendorfs at 6000 rpm. The PROH supernatant was removed and the precipitate redissolved in 1 ml of 10 mM Tris-HCl buffer (pH 7.8) containing 1 mM EDTA and 1 mM NaCl.

Comparison

The UV spectrum of the precipitate was compared with a sample of the original DNA dissolved at the same concentration of 0.5 unit/ml in 1 ml of 10 mM Tris-HCl buffer (pH 7.8) containing 1 mM EDTA and 1 mM NaCl.

From bottle as received from Sigma: Abs at 260 nm=0.421, Abs at 280 nm=0.219.

After redissolution of precipitate in buffer. Abs at 260 nm=0.415, Abs at 280 nm=0.237.

This shows that the precipitation process is very efficient with little or no loss of DNA.

The invention claimed is:

1. A method of preparing water soluble particles comprising a coprecipitant core with a dehydrated biological macromolecule coated thereon comprising the steps of:
    a) preparing an aqueous solution comprising a coprecipitant and a biological macromolecule wherein the coprecipitant core consists of one of the following of inorganic salts; sugars, polyols, and derivatives thereof with a molecular weight less than 10,000 Da; aminoacids; acid-base buffers; zwitterionic compounds; organic salts; compounds containing multiple basic groups; compounds containing multiple acidic groups; bile salts; and, water soluble dyes;
    b) rapidly admixing the biological macromolecule/coprecipitant solution with an excess of a water miscible organic solvent such that the coprecipitant and bioactive molecule immediately coprecipitate from solution forming said particles; and
    c) isolating said particles from the organic solvent.

2. The method according to claim 1 wherein the aqueous solution comprising the coprecipitant and the biological macromolecule is prepared by dissolving the coprecipitant in an aqueous solution comprising the biological macromolecule.

3. The method according to either of claim 1 wherein the biological macromolecule/coprecipitant solution is added to the water miscible organic solvent.

4. The method according to claim 1 wherein the coprecipitant biological macromolecule molar ratio is greater than 50.

5. The method according to claim 1 wherein the organic solvent is selected from methanol, ethanol, propanol, acetonitrile, tetrahydrofuran and acetone.

6. Particles obtainable by the process according to claim 1.

7. A pharmaceutical formulation comprising particles according to claim 6 and a suitable carrier therefore.

8. A medical device comprising particles according to claim 6 associated therewith.

9. Particles according to claim 6 for use in therapy.

10. A biocatalyst preparation comprising particles according to claim 6 associated therewith.

11. A cleansing agent comprising enzyme coated particles according to claim 6.

12. A protective or antifouling agent comprising particles according to claim 6 in association with paint, varnish, coatings or films.

13. Films, polymers, inks, coatings, electrodes and optical materials for diagnostic kits or biosensor applications, comprising particles according to claim 6.

14. A method for studying molecular recognition, molecular binding, molecular imprinting or inhibitor binding in non-aqueous media, comprising using particles according to claim 6.

15. A method for studying macromolecule structure and/or organisation by scanning probe microscopy, comprising using particles according to claim 6.

16. The method according to claim 1 wherein said coprecipitant core is a non-polymeric core.

* * * * *

UNITED STATES PATENT AND TRADEMARK OFFICE
CERTIFICATE OF CORRECTION

PATENT NO. : 7,014,869 B2  Page 1 of 1
APPLICATION NO. : 10/007257
DATED : March 21, 2006
INVENTOR(S) : Moore et al.

It is certified that error appears in the above-identified patent and that said Letters Patent is hereby corrected as shown below:

Column 14,
Line 23, after "soluble particles", insert --of less than 50 µm--;
Line 45, after "according to", cancel "either of".

Signed and Sealed this

Eighth Day of August, 2006

JON W. DUDAS
*Director of the United States Patent and Trademark Office*